United States Patent [19]
Mitsuhashi et al.

[11] Patent Number: 4,849,225
[45] Date of Patent: * Jul. 18, 1989

[54] PROCESS TO PREPARE SOLID PRODUCTS CONTAINING OIL-SOLUBLE SUBSTANCE

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[ * ] Notice: The portion of the term of this patent subsequent to Feb. 7, 2005 has been disclaimed.

[21] Appl. No.: 70,138

[22] Filed: Jun. 29, 1987

[30] Foreign Application Priority Data

Jul. 10, 1986 [JP] Japan .................. 61-162656

[51] Int. Cl.$^4$ ............................................. A61K 47/00
[52] U.S. Cl. ................................. 424/439; 421/440; 421/441; 421/499; 421/502; 426/531; 426/549; 426/660; 426/658; 426/605; 426/589; 426/618; 426/557; 426/92; 426/601; 426/564; 426/654; 426/662

[58] Field of Search ............... 421/451; 424/439, 440, 424/441, 499; 426/531, 549, 660, 658, 605, 658, 557, 92, 601, 564, 654, 662

[56] References Cited

U.S. PATENT DOCUMENTS 4,408,041 10/1983 Hirao et al. ..................... 424/48

OTHER PUBLICATIONS

Peat et al., *J. Chem. Soc.*, pp. 714–437 (1952).

*Primary Examiner*—Thurman K. Page
*Assistant Examiner*—Leon R. Horne
*Attorney, Agent, or Firm*—Browdy and Neimark

[57] ABSTRACT

Disclosed is a novel process to prepare a solid product containing an oil-soluble substance (e.g. oil and fat, spice, flavor, vitamin, emulsifier, hormone, higher fatty acid, unsaponifiable substance and complex lipid), comprising adding to an oil-soluble liquid substance an anhydrous maltose (e.g. anhydrous crystalline alpha-maltose, anhydrous crystalline beta-maltose and anhydrous amorphous maltose) along with water, and crystallizing beta-maltose hydrate in the mixture.

11 Claims, No Drawings

PROCESS TO PREPARE SOLID PRODUCTS CONTAINING OIL-SOLUBLE SUBSTANCE

BACKGROUND OF THE INVENTION
1. Field of the invention

The present invention relates to a process to prepare solid products containing an oil-soluble substance, in particular, to that wherein an oil-soluble liquid substance is added with water and anhydrous maltose which is then crystallized in beta-maltose hydrate form.

2. Definitions and abbreviation

In the specification, percentages and parts will be expressed by weight unless specified otherwise, and dry solid basis is abbreviated as "d.s.b.".

3. Description of the prior art

Solidification using saccharides has been variously attempted to prepare oil-soluble liquid substances into solid products.

Japanese Patent Laid-Open No. 104,998/81 discloses that oil and fat are pulverable by adding water to a saccharide including glucose or lactose, heating the resultant mixture at 100°–140° C. into a porous amorphous granule, and admixing thereto an oil-soluble liquid substance such as salad oil.

This method has the drawback that it leads to a highly hygroscopic, colored product because the saccharides are exposed to a relatively high temperature.

Japanese Patent Laid-Open No. 214,845/85 discloses that lecithin is pulverable by heating a mixture of starch and lecithin together with a large amount of water to 110°–140° C., and spray-drying the resultant.

This method has the drawbacks that it deteriorates or alters lecithin because it heats lecithin with water at relatively high temperature and pressure, as well as that it consumes a relatively large amount of energy.

SUMMARY OF THE INVENTION

In view of the foregoing, we investigated the possibility of using maltose to prepare oil-soluble substances into solid product in order to overcome these drawbacks of conventional method.

As the result, we found that anhydrous maltose, particularly, that having a maltose content of 85% or higher, d.s.b., acts as a solidifying agent for an oil-soluble liquid substance when added together with water and crystallized in beta-maltose hydrate form; as well as that a high-quality solid product containing the oil-soluble substance is easily obtainable by utilizing this property.

DETAILED DESCRIPTION OF THE INVENTION

The oil-soluble liquid substances as referred to in the invention are oily solvent-soluble liquids; for example, oils and fats such as soybean oil, rapeseed oil, mustard oil, sesame oil, safflower oil, cottonseed oil, palm oil, cacao butter, beef tallow, lard, chicken oil, marine oil, bone oil and hardened oil; oil-soluble flavors and spices such as citrus essential oil, flower essential oil, spice oil, peppermint oil, spearmint oil, cola nut extract and coffee extract; oil-soluble coloring agent such as beta-carotin, paprika pigment, annatto pigment and chlorophyll; oil-soluble vitamins such as liver oil, vitamin A, vitamin $B_2$ lactate, vitamin E, vitamin K and vitamin D; oil-soluble hormones such as estrogen, progesterone and androgen; unsaturated higher fatty acids such as linoleic acid, linolenic acid, arachidonic acid, eicosapentaenoic acid and docosahexaenoic acid; unsaponifiable substances such as higher alcohol, sterol and squalene; and complex lipids such as lecithin and cephalin.

The physical properties and processibility of an oil-soluble substance having a relatively high melting point, for example, hardened oil, essential oil, sterol, higher alcohol or wax, are improved first by melting it by heating or dissolving in a solvent such as alcohol, chloroform or ether; then adding anhydrous maltose and water to the resultant liquid or solution to effect solidification. In this way, the use of such oil-soluble substances can be expanded.

The present invention is advantageously applicable to oil-soluble liquid substances having a decreased moisture content, particularly, lower than 5%, more particularly, lower than 2%.

We found that a high-purity maltose with a maltose content of 85% or higher, d.s.b., is suitable for the anhydrous maltose because it readily crystallizes in beta-maltose hydrate form even in the presence of an oil-soluble substance.

Such high-purity maltose may be a commercialized crystalline beta-maltose hydrate or that obtained by saccharifying starch in conventional manner.

As to such saccharification, Japanese Patent Publication Nos. 11,437/81 and 17,078/81 disclose that a gelatinized- or liquefied-starch is subjected to the action of beta-amylase to form maltose which is then separated from the concomitant maltodextrins; and Japanese Patent Publication Nos. 13,089/72 and 3,983/79 disclose that a gelatinized- or liquefied-starch is subjected to the actions of starch-debranching enzyme, such as pullulanase or isoamylase, and beta-amylase.

The maltose content of the obtained product can be augmented by subjecting the concomitant saccharides including maltotriose to an enzyme as disclosed, for example, in Japanese Patent Publication Nos. 28,153/81, 3,356/82 and 28,154/81, to form maltose; or separating the saccharides by the fractionation as disclosed in Japanese Patent Laid-Open No.23,799/83 using a strongly-acidic cation exchange resin in a salt form. The fractionation is carried out by the fixed bed-, moving bed-, or simulating moving bed-method.

The following is illustrative of preparing anhydrous maltose from the high-purity maltose obtained in this way.

The preferred forms of anhydrous maltose include anhydrous crystalline alpha-maltose, anhydrous crystalline beta-maltose, and anhydrous amorphous maltose.

As disclosed in Japanese Patent Laid-Open No. 35,800/86, anhydrous crystalline maltose powder is prepared, for example, by providing from a high-purity maltose a syrup with a moisture content lower than about 10%, desirably, 2.0% or higher but lower than 9.5%; crystallizing alpha-maltose by keeping the syrup at a temperature in the range of 50°–130° C.; and pulverizing the resultant crystalline alpha-maltose.

Anhydrous crystalline beta-maltose powder is prepared, for example, by vacuum-drying a crystalline beta-maltose hydrate powder under conditions where it does not melt, for example, a temperature of about 80°–110° C.

Amorphous anhydrous maltose is prepared, for example, from a commercialized crystalline beta-maltose hydrate, or from an aqueous solution of a high-purity maltose having a maltose content of 85% or higher, d.s.b. In the case of using a commercialized crystalline beta-maltose hydrate, it is dehydrated at normal or a reduced pressure under conditions where it melts, for example, a temperature of about 120°–150° C., followed by pulverization. In the case of using an aqueous solution of a high-purity maltose, the aqueous solution is prepared into a syrup with a concentration of about 70–95%, which is then vacuum- or freeze-dried, followed by pulverization. Alternatively, the aqueous solution is prepared into a syrup with a concentration of about 50–85%, and then spray-dried directly into powder with a high pressure nozzle or a rotary disc.

The anhydrous maltose thus obtained is a white powder having a mild, reduced sweetness. Its moisture is extremely low or substantially anhydrous. The Karl Fischer's method gave a moisture content, usually, lower than 3%, desirably, lower than 2%. Anhydrous maltose is substantially free-flowing, but this slightly varies with the particle shape and size.

The wording "anhydrous maltose" as referred to in the invention means a substantially anhydrous maltose that is convertible into beta-maltose hydrate form in the presence of water to exert an ability of solidifying an oil-soluble liquid substance. A substantially anhydrous amorphous maltose powder wherein a minimum amount of crystalline beta-maltose hydrate seed, generally, less than 5%, desirably, less than 1%, d.s.b., has been added may be used to accelerate the conversion and also to improve the ability.

We found that an anhydrous maltose, added together with a relatively small amount of water to an oil-soluble liquid substance, for example, oil and fat, oil-soluble flavor, oil-soluble coloring agent, oil-soluble vitamin, oil-soluble emulsifier and oil-soluble hormone, swells about 1.2-folds or more, occasionally, about 1.5- to 4.0-folds while including a large amount of the oil-soluble substance as the conversion into crystalline beta-maltose hydrate proceeds. We confirmed that this renders anhydrous maltose an advantageously usable material for solidifying oil-soluble liquid substances.

The weight ratio of anhydrous maltose to oil-soluble liquid substance is 0.10–500, desirably, 0.20–50.0.

The amount of water to that of anhydrous maltose is 1.0–30.0%, desirably, 2.0–25.0%. The water may be attained with a steam or a moisture absorption in a highly humid atmosphere, and should not be restricted to that in liquid or solution.

Anhydrous maltose and water are added to an oil-soluble liquid substance in conventional manner during the preparation of solid product, for example, mixing, kneading, dissolving, permeating, sprinkling, applying, spraying, and injecting.

The following will illustrate the present invention much more concretely.

Crystallization of beta-maltose hydrate is attained by adding an appropriate amount of water to either or both an oil-soluble liquid substance and anhydrous maltose, mixing them, and ageing the mixture by allowing it to stand at ambient temperature. In this case, the intake of the oil-soluble substance occurs homogeneously without release to give a solid product.

Alternatively, an oil-soluble liquid substance is mixed with anhydrous maltose, and the resultant is added with an appropriate amount of water, and aged similarly as above.

In either case, one or more of flavor, coloring agent, seasoning, surface active agent, antioxidant, stabilizer and filler may be used in combination. The stabilizer and filler include water-soluble polymers, for example, solubilized starch, dextrin, cyclodextrin, pullulan, elsinan, dextran, xanthan gum, gum arabic, locust bean gum, guar gum, tragacanth gum, tarmalind gum, carboxymethyl cellulose, hydroxyethyl cellulose, pectin, agar, gelatin, albumin and casein.

The present invention is variously practiced in the preparation of solid products containing an oil-soluble substance, particularly, those in powder. For example, anhydrous maltose and water are added to an oil-soluble liquid substance as described above, and the mixture is placed in a tray, and solidified, for example, into block while accelerating the crystallization of beta-maltose hydrate by allowing the mixture to stand at about 10°–50° C. for about 0.1–10 days. The block is pulverized by cutting and scraping, followed by drying and/or sieving, if necessary. Powder and granule are directly preparable with spray-drying or wet granulation.

In the case of the spray-drying, a predetermined amount of an oil-soluble liquid substance containing an appropriate amount of water is granulated by spraying it towards a fluidizing anhydrous maltose powder, and then aged at about 30°–60° C. for 1–24 hours while accelerating the crystallization of beta-maltose hydrate. Alternatively, a powder, obtained by mixing or kneading an oil-soluble liquid substance together with anhydrous maltose and water, and spraying the resultant, is aged similarly as above while accelerating the crystallization of beta-maltose hydrate. Thus, a stable powder is obtained.

In the case of the wet granulation, an oil-soluble liquid substance is fed to a granulator, for example, mixer or crystallizer, and mixed with anhydrous maltose and an appropriate amount of water by stirring, and the resultant is granulated and aged while accelerating the crystallization of beta-maltose hydrate. Thus, a stable granule is obtained.

In either case, the ageing period is shortened by adding a small amount of crystalline beta-maltose hydrate seed to accelerate the crystallization of beta-maltose hydrate.

The pulverulent product thus obtained is usable alone or, if necessary, in combination with one or more of filler, vehicle, binder and stabilizer. The product may be shaped into granule, tablet, capsule, rod, plate or cube, prior to its use.

The product is a high-quality, non-hygroscopic and stable solid free of browning, coloring, volatilization of flavors, alteration or deterioration of effective ingredients because its preparation involves no vigorous heating step.

The product is extensively usable, for example, as or in flavoring agents, coloring agents, emulsifying agents, food products, pharmaceuticals, cosmetics, toiletries, and intermediates thereof, dependently on the properties of the oil-soluble substances.

The following Examples for Reference are illustrative of preparing powdery anhydrous maltose.

EXAMPLE OF REFERENCE 1

A suspension of one part of potato starch in ten parts of water was added with a commercialized bacterial liquefying alpha-amylase, and the mixture was heated to 90° C. to effect liquefaction. The enzymatic reaction was suspended by heating the mixture to 130° C., thus a liquefied starch solution having a Dextrose Equivalent (DE) of about 0.5 was obtained. Thereafter, the starch solution was quickly cooled to 55° C., and added with 100 units/g starch solid of isoamylase (EC 3.2.1.68)

prepared from a culture of *Pseudomonas amyloderamosa* ATCC 21262, along with 50 units/g starch solid of beta-amylase (EC 3.2.1.2) derived from soybean, commercialized by Nagase & Company, Ltd., Osaka, Japan, under the trade name of "#1500". The starch in the mixture was saccharified by incubation at 55° C. and pH 5.0 for 40 hours to obtain a solution having a maltose content of 92.5%, d.s.b. The solution was decolored with activated carbon, deionized with ion exchange resins, concentrated to 75%, fed to a crystallizer, added with 1% of crystalline beta-maltose hydrate seed powder, d.s.b., adjusted to 40° C., and cooled to 30° C. over a period of two days with a gradual stirring. The crystal, recovered from the resultant massecuite with a basket-type centrifuge, was washed by spraying thereto a minimum amount of water to obtain a crystalline beta-maltose hydrate having a maltose purity of 99.0%, d.s.b.

The crystalline beta-maltose hydrate was dissolved in a small amount of water by heating, and the resultant solution was placed in an evaporator, and boiled in vacuo into a syrup with a moisture content of 5.5%. The syrup was placed in a crystallizer, added with 1% of anhydrous crystalline alphamaltose, d.s.b., obtained by the method as disclosed in Japanese Patent Laid-Open No.35,800/86, in Test No.6 of Experiment 1, crystallized at 100° C. for five minutes, placed in a plastic tray, and aged at 70° C. for six hours to obtain a block.

The block was fed to a pulverizer, and subjected to a fluidized bed drying to obtain an anhydrous crystalline alphamaltose powder, alpha-maltose isomer content of 73.3%, d.s.b., moisture content of 0.42%, in the yield of about 92% against the starting crystalline beta-maltose hydrate.

The product is advantageously usable as a white sweetener powder having a mild sweetness, as well as to solidify oil-soluble liquid substances.

EXAMPLE FOR REFERENCE 2

An aqueous solution of a high-purity maltose having a maltose content of 92.5%, d.s.b., prepared by the method in Example for Reference 1, was concentrated in vacuo to give a moisture content of 20%, and sprayed from the top of a spray-drying tower through nozzle with a high pressure pump in a 100° C. air stream towards a crystalline alpha-maltose powder fluidizing on a mesh equipped to a conveyor while supplying 70° C. air upwardly through the mesh, gradually conveyed outside the tower over a period of 60 minutes to an ageing tower, and aged for four hours in a 70° C. air stream to obtain an anhydrous crystalline alpha-maltose powder, alpha-maltose isomer content of 66.2%, d.s.b., moisture content of 0.55%, in the yield of about 94% against the starting crystalline beta-maltose hydrate.

Similarly as the product in Example for Reference 1, the product is advantageously usable as a sweetener, as well as to solidify oil-soluble liquid substances.

EXAMPLE FOR REFERENCE 3

A suspension of two parts of cornstarch in ten parts of water was added with a commercialized bacterial liquefying alpha-amylase, and the mixture was heated to 90° C. to effect liquefaction. The enzymatic reaction was suspended by heating the mixture to 130° C., thus a liquefied starch solution having a DE of about 2 was obtained. Thereafter, the liquefied starch solution was quickly adjusted to 55° C., and added with 120 units/g starch solid of isoamylase (EC 3.2.1.68), prepared from a culture of *Pseudomonas amyloderamosa* ATCC 21262, along with 30 units/g starch solid of beta-amylase (EC 3.2.1.2) derived from soybean. The starch in the mixture was saccharified by incubation at 55° C. and pH 5.0 for 36 hours, and the resultant was purified similarly as in Example for Reference 1 to obtain a high-purity maltose solution with a maltose content of 88.6%, d.s.b., which was then concentrated in vacuo into a syrup having a moisture content of 3.5%.

The syrup was placed in a crystallizer, added with an anhydrous crystalline alpha-maltose, prepared by the method in Example for Reference 2, in an amount of 2.5%, d.s.b., crystallized at 120° C. for ten minutes, placed in an aluminum tray, aged at 70° C. for 18 hours, pulverized and dehydrated similarly as in Example for Reference 1 to obtain an anhydrous crystalline alpha-maltose powder, alpha-maltose isomer content of 63.9%, d.s.b., moisture content of 0.60%, in the yield of about 94% against the starting high-purity maltose.

Similarly as the product in Example for Reference 1, the product is advantageously usable as a sweetener, as well as to solidify oil-soluble liquid substances.

EXAMPLE FOR REFERENCE 4

A feed solution was prepared by dissolving "HM-75", a starch syrup having a maltose content of 79.6%, d.s.b., commercialized by Hayashibara Co., Ltd., Okayama, Japan, in water to give a concentration of 45%. "XT-1022E ($Na^+$-form)", a strongly-acidic cation exchange resin commercialized by Tokyo Chemical Industries, Tokyo, Japan, was packed in aqueous suspension in four 5 m jacketed stainless steel columns, diameter of 5.4 cm, and the columns were cascaded to give a total column depth of about 20 m.

While keeping the temperature inside the columns at 55° C., the feed solution was applied to the cascade in an amount of 5% by volume of the resin, and a 55° C. water was admitted in the columns at a flow rate of SV 0.13 to effect fractionation. From the resultant maltose-rich fraction was recovered a maltose solution having a maltose content of 94.4%, d.s.b.

The maltose solution, obtained by repeating the above operation twenty times, was concentrated in vacuo to obtain a syrup having a moisture content of 4.0% which was then placed in a crystallizer, added with 2.0% of an anhydrous crystalline alpha-maltose seed, d.s.b., obtained by the method in Example for Reference 1, crystallized at 110° C. for 20 minutes, and fed to a screw-type extrusion granulator. The resultant granule was placed in a dehydrating chamber, and aged in an 80° C. air stream for two hours to obtain an anhydrous crystalline alphamaltose powder, alpha-maltose isomer content of 69.2%, d.s.b., moisture content of 0.48%, in the yield of about 93% against the starting high-purity maltose.

Similarly as the product in Example for Reference 1 the product is advantageously usable as a sweetener, as well as to solidify oil-soluble liquid substances.

EXAMPLE FOR REFERENCE 5

A crystalline beta-maltose hydrate, obtained by the method in Example for Reference 1, was vacuum-dried at 95° C. for two days to obtain an anhydrous crystalline beta-maltose powder having a moisture content of 0.36%.

Similarly as the product in Example for Reference 1, the product is usable as a sweetener, as well as to solidify oil-soluble liquid substances.

EXAMPLE FOR REFERENCE 6

An aqueous solution of a high-purity maltose, obtained by the method in Example for Reference 3, was concentrated in vacuo to give a moisture content of 25%, and sprayed downwards from the top of a spray-drying tower through a nozzle with a high pressure pump into a 160° C. air stream to effect dehydration. The resultant powder was collected at the bottom of the tower, and conveyed outside the tower to obtain a powder having a moisture content of 0.40%. The powder was admixed with about 0.1% of a crystalline beta-maltose hydrate seed, d.s.b., obtained by the method in Example for Reference 1, to obtain a substantially anhydrous amorphous maltose powder.

Similarly as the product in Example for Reference 1, the product is advantageously usable as a sweetener, as well as to solidify oil-soluble liquid substances.

EXAMPLE FOR REFERENCE 7

An aqueous solution of a high-purity maltose, obtained by the method in Example for Reference 4, was concentrated in vacuo to give a moisture content of 30%, and spray-dried similarly as in Example for Reference 6 to obtain an anhydrous amorphous maltose powder having a moisture content of 0.45%.

Similarly as the product in Example for Reference 1, the product is advantageously usable as a sweetener, as well as to solidify oil-soluble liquid substances.

Several embodiments and superior effects of the present invention will hereinafter be described.

EXAMPLE 1

Powder containing salad oil

One-hundred and fifty parts of soybean salad oil was mixed with 13 parts of water at ambient temperature, and the mixture was added with 100 part of an anhydrous maltose obtained by the method in Example for Reference 1. The resultant was placed in a tray and solidified into block, and the block was aged while accelerating the crystallization of beta-maltose hydrate by allowing it to stand at ambient temperature for two days.

The block was then fed to a pulverizer, and the resultant was sieved to obtain a high-quality powder containing salad oil.

The product was advantageously usable for preparing confectioneries such as premix, frozen dessert, cake and candy; foods such as mayonnaise, dressing, potage soup, stew and "chahan (mixed fried rice)"; medicines for promoting nutrition such as intubation feeding; and feeds.

EXAMPLE 2

Granule containing "rayu (a hot oil made from sesame oil and cayenne pepper)"

Ninety-five parts of rayu was mixed with 95 parts of an anhydrous maltose obtained by the method in Example for Reference 2, and the mixture was added with 12 parts of water at ambient temperature. The resultant was solidified, aged, pulverized similarly as in Example 1, and fed to a granulator to obtain a granule excellent in taste and flavor.

The product is advantageously usable as a seasoning for Chinese dishes such as "ramen (Chinese noodle)", instant ramen, "gyoza (a fried dumpling stuffed with minced pork)", and "wantan (a Chinese flour dumpling with pork)".

EXAMPLE 3

Powder containing bone oil

One hundred parts of bone oil was mixed with 11 parts of water, and the mixture was added with 80 parts of an anhydrous maltose obtained by the method in Example for Reference 3. The resultant was solidified, aged by allowing it to stand at ambient temperature for two days, fed to a pulverizer, and dried by one-day ventilation at ambient temperature.

The product is advantageously usable as or in health-promoting agent, tonic, cosmetic and feed intact or after shaped into granule or tablet.

EXAMPLE 4

Powder containing shortening

One hundred parts of shortening was mixed with 100 parts of an anhydrous maltose obtained by the method in Example for Reference 6, and the mixture was added with 15 parts of water. The resultant was sprayed downwards from the top of a spray-drying tower through a nozzle with a high pressure pump in a 50° C. air stream. The resultant powder was collected at the bottom of the tower, placed in an ageing tower, and aged at 30° C. overnight to obtain a high-quality powder containing shortening.

Similarly as the product in Example 1, the product is advantageously usable in confectioneries, cooked products, medicines for promoting nutrition, and feeds.

EXAMPLE 5

Sandwiched cream

One thousand parts of shortening was mixed with 1,100 parts of an anhydrous maltose obtained by the method in Example for Reference 2, one part of lecithin, one part of lemon flavor, and one part of vanilla oil in usual manner, and the resultant mixture was poured into shallow trays placed on a conveyor to give a depth of about 5 mm, passed through a humidified chamber over a period of one hour, solidified, aged by allowing it to stand at ambient temperature overnight, removed from the trays, and packed to obtain a sandwiched cream excellent in taste and flavor.

The product is advantageously usable as or in confectioneries intact or after pulverization.

EXAMPLE 6

Chocolate tablet

Forty parts of cacao paste and five parts of cacao butter were mixed with 55 parts of an anhydrous maltose obtained by the method in Example for Reference 4, and 0.2 parts of "α-G-Sweet", an alpha-glycosyl stevioside sweetener commercialized by Toyo Sugar Refining Co., Ltd., Tokyo, Japan, and the mixture was fed to a refiner to pulverize it to homogeneity, added with 0.3 parts of lecithin, kneaded with a conche, and added with six parts of water. The resultant was placed in a tray, solidified into block, and aged by allowing it to stand at ambient temperature.

The block was fed successively to a pulverizer and a tabletting machine, sugar-coated and polished to obtain a tablet.

The product is excellent in taste and flavor, and free of causing deformation and cracking.

EXAMPLE 7

Powder containing lecithin

Sixty parts of egg lecithin was mixed with nine parts of water, and the resultant mixture was added with 100 parts of an anhydrous maltose obtained by the method in Example for Reference 5. The resultant was solidified, aged and pulverized similarly as in Example 1.

The product having a strong emulsifying power is advantageously usable as or in emulsifying agent for oils and fats; foaming agent for confectioneries such as sponge cake, cookie and biscuit; emulsion stabilizer; agent to improve the quality of oily food products, noodle, vermicelli and creams; and cosmetic.

EXAMPLE 8

Powder containing squalene

One-hundred and twenty parts of squalene was mixed with 100 parts of an anhydrous maltose obtained by the method in Example for Reference 1, and the resultant mixture was added with 12 parts of water. The resultant was solidified, aged and pulverized similarly as in Example 1.

The product is advantageously usable in health foods and cosmetics.

EXAMPLE 9

Granule containing menthol

Two-hundred and sixteen parts of L-menthol and 43.2 parts of eucalyptus oil were dissolved in 100 parts of ethyl alcohol, and the resultant solution was added with 800 parts of an anhydrous maltose obtained by the method in Example for Reference 3. The resultant was granulated by spraying thereto 105 parts of a peppermint liquor, moisture content of about 50%, with stirring.

The product is advantageously usable for flavoring hard candy, chewing gum, frozen dessert, and confectionery in tablet.

EXAMPLE 10

Granule containing eicosapentaenoic acid

Four parts of eicosapentaenoic triglyceride was mixed with ten parts of a partial starch hydrolysate containing cyclodextrins, moisture content of about 25%, and the mixture was added with 55 parts of an anhydrous maltose obtained by the method in Example for Reference 7. The resultant was granulated by spraying thereto a small amount of water.

The eicosapentaenoic acid in the product is very stable because it forms an inclusion compound together with cyclodextrins.

The product is advantageously usable in health foods and pharmaceuticals wherein eicosapentaenoic acid provides anticholesteremic- and arteriosclerosis preventing-activities.

EXAMPLE 11

Vitamin A tablet

One hundred parts of vitamin A palmitate was mixed with 100 parts of an anhydrous maltose obtained by the method in Example for Reference 6, and the mixture was added with 13 parts of water. The resultant was solidified, aged and pulverized similarly as in Example 1.

A mixture of one part of the powder and one part of cornstarch was fed to a tabletting machine, and the resultant were sugar-coated and polished in conventional manner.

The product containing a high titer of vitamin A palmitate is advantageously usable in health foods and pharmaceuticals.

The product is stable and free of deformation or cracking.

As obvious from the above, the present invention relates to a process to prepare solid products containing an oil-soluble substance, particularly, to that wherein an anhydrous maltose, added together with and water to an oil-soluble liquid substance, for example, oil and fat, oil-soluble flavor, oil-soluble coloring agent, and oil-soluble emulsifier, is crystallized in beta-maltose hydrate form while allowing it to take in a relatively large amount of the oil-soluble substance.

Since the process contains no vigorous processing step, it causes no deterioration or alteration of the taste, flavor and effective ingredient(s) of an oil-soluble liquid substance. Thus, a high-quality solid product is easily obtainable.

The product thus obtained is advantageously usable in flavoring agents, coloring agents, emulsifying agents, cosmetics, toiletries, and intermediates thereof.

While the preferred forms of the present invention have been described, it is to be understood that modifications will be apparent to those skilled in the art without departing from the spirit of the invention.

The scope of the invention, therefore, is to be determined solely by the following claims.

We claim:

1. A process to prepare a solid product containing an edible oil-soluble substance, comprising:
   adding anhydrous maltose and water to an oil-soluble liquid substance; and
   crystallizing beta-maltose hydrate in the mixture.

2. The process of claim 1, wherein said edible oil-soluble substance is a low-moisture content edible oil-soluble substance.

3. The process of claim 1, wherein said anhydrous maltose has a maltose content of 85% by weight or higher based on the dry solid.

4. The process of claim 1, wherein said anhydrous maltose is in pulverulent form.

5. The process of claim 1, wherein the moisture content of said anhydrous maltose is lower than 3% by weight.

6. The process of claim 1, wherein cyclodextrin is added together with the anhydrous maltose.

7. The process of claim 1, wherein said anhydrous maltose is a member selected from the group consisting of anhydrous crystalline alpha-maltose, anhydrous crystalline beta-maltose, amorphous maltose, and mixtures thereof.

8. The process of claim 1, wherein the weight ratio of the edible oil-soluble substance to the anhydrous maltose is in the range of from 1.0:0.10 to 1.0:500.

9. The process of claim 1, wherein the amount of water to anhydrous maltose is in the range of 1.0 to 30.0% by weight.

10. The process of claim 1, wherein said solid product is in the form of powder, granule, tablet, capsule, rod or plate.

11. The process of claim 1, wherein said solid product is a member selected from the group consisting of flavoring agent, coloring agent, emulsifying agent, food product, pharmaceutical, cosmetic, toiletries, materials and intermediates thereof.

* * * * *